US009330944B2

(12) United States Patent
Smith et al.

(10) Patent No.: US 9,330,944 B2
(45) Date of Patent: May 3, 2016

(54) BIO-IMPLANTABLE HERMETIC INTEGRATED ULTRA HIGH DENSITY DEVICE

(71) Applicant: The Charles Stark Draper Laboratory, Inc., Cambridge, MA (US)

(72) Inventors: Brian R. Smith, Cambridge, MA (US); Tirunelveli S. Sriram, Acton, MA (US); Bryan L. McLaughlin, Cambridge, MA (US)

(73) Assignee: THE CHARLES STARK DRAPER LABORATORY, INC., Cambridge, MA (US)

(*) Notice: Subject to any disclaimer, the term of this patent is extended or adjusted under 35 U.S.C. 154(b) by 0 days.

(21) Appl. No.: 14/959,647

(22) Filed: Dec. 4, 2015

(65) Prior Publication Data

US 2016/0086824 A1 Mar. 24, 2016

Related U.S. Application Data

(62) Division of application No. 13/490,189, filed on Jun. 6, 2012, now Pat. No. 9,224,664.

(51) Int. Cl.

*H05K 3/30* (2006.01)
*H05K 7/00* (2006.01)
*H01L 21/56* (2006.01)
*H01L 21/768* (2006.01)
*A61N 1/372* (2006.01)

(52) U.S. Cl.

CPC ............ *H01L 21/56* (2013.01); *A61N 1/37205* (2013.01); *H01L 21/76895* (2013.01)

(58) Field of Classification Search

CPC ............ H05K 3/30; H05K 7/00; H05K 3/284
USPC ........... 361/760; 607/116–119; 257/685, 686, 257/774, 787
See application file for complete search history.

(56) References Cited

U.S. PATENT DOCUMENTS 7,890,165 B2 2/2011 Wahlstrand et al.
8,017,451 B2 9/2011 Racz et al.
8,273,603 B2 9/2012 Racz et al.

(Continued)

OTHER PUBLICATIONS

International Preliminary Report on Patentability mailed Dec. 18, 2014 in PCT Application No. PCT/US2013/043896.

(Continued)

*Primary Examiner* — Jenny L Wagner
*Assistant Examiner* — Michael P McFadden
(74) *Attorney, Agent, or Firm* — Edward A. Gordon; Foley & Lardner LLP

(57) ABSTRACT

An implantable bio-compatible integrated circuit device and methods for manufacture thereof are disclosed herein. The device includes a substrate having a recess. An input/output device including at least one bio-compatible electrical contact is coupled to the substrate in the recess. A layer of hermetic bio-compatible, hermetic insulator material is deposited on a portion of the input/output device. An encapsulating layer of bio-compatible material encapsulates at least a portion of the implantable device, including the input/output device. At least one bio-compatible electrical contact of the input/output device is then exposed. The encapsulating layer and the layer of bio-compatible, hermetic insulator material form a hermetic seal around the at least one exposed bio-compatible electrical contact.

10 Claims, 18 Drawing Sheets

100a
102 130 134 128 126 120a 120b 120c 134
111a 111b 111c 111d 111e 111f
118 116 110 118 116 112 118 116 114 118

(56) References Cited

U.S. PATENT DOCUMENTS

| | | | | |
|---|---|---|---|---|
| 8,535,984 | B2 | 9/2013 | Racz et al. | |
| 2007/0235216 | A1 | 10/2007 | Bae et al. | |
| 2010/0168818 | A1 | 7/2010 | Barror et al. | |
| 2010/0262208 | A1 | 10/2010 | Parker | |
| 2010/0265680 | A1 | 10/2010 | Tai et al. | |
| 2011/0004283 | A1* | 1/2011 | Stevenson ................ | H01G 4/40 607/116 |
| 2011/0034977 | A1* | 2/2011 | Janik ........................ | A61N 1/05 607/116 |
| 2011/0077699 | A1 | 3/2011 | Swanson et al. | |
| 2012/0107999 | A1 | 5/2012 | Fan | |
| 2012/0209100 | A1 | 8/2012 | De Beeck et al. | |

OTHER PUBLICATIONS

International Search Report and Written Opinion for PCT/US2013/043896 mail dated Sep. 24, 2013.

US Notice of Allowance in U.S. Appl. No. 13/490,189 DTD Aug. 28, 2015.

US Office Action in U.S. Appl. No. 13/490,189 DTD Oct. 23, 2014.

US Office Action in U.S. Appl. No. 13/490,189 DTD Feb. 18, 2014.

US Office Action in U.S. Appl. No. 13/490,189 DTD Apr. 9, 2015.

* cited by examiner 200b
228
226
220b
234
211a
211b
220a
230
228
226
202
218
216
212
230

BIO-IMPLANTABLE HERMETIC INTEGRATED ULTRA HIGH DENSITY DEVICE

RELATED APPLICATIONS

This application is a divisional of, and claims the benefit of and priority to, U.S. patent application Ser. No. 13/490,189, titled "BIO-IMPLANTABLE HERMETIC INTEGRATED ULTRA HIGH DENSITY DEVICE" and filed on Jun. 6, 2012, the entire contents of which are hereby incorporated by reference in their entirety.

FIELD OF THE INVENTION

In general, the invention relates to systems and methods for construction of bio-compatible hermetic integrated Ultra High Density (iUHD) integrated circuit-based devices.

BACKGROUND OF THE INVENTION

A standard implantable medical device is typically surface mounted onto a printed circuit board and enclosed in a bio-compatible volume, usually a titanium can. These devices are often bulky and invasive to the body. Surgeries involving implantable medical devices are prone to complications and pose risks to the patient such as infections, allergic reactions, swelling, bruising, bleeding, damage to blood vessels or nerves near the device, or even rejection of the device. The risk of such complications can become significant when the implantable device is large. Therefore, it is desirable to have smaller bio-compatible implantable devices to reduce these risks. Furthermore, having small bio-compatible implantable devices allows for a greater selection of implant locations. A smaller implantable device may be implanted at a site where larger implants would not fit or would introduce complications at increased risks.

SUMMARY

The systems disclosed herein include an implantable bio-compatible integrated circuit device. The device includes a substrate having a recess. An input/output device including at least one bio-compatible electrical contact is coupled to the substrate in the recess. A layer of bio-compatible, hermetic insulator material is deposited on a portion of the input/output device. An encapsulating layer of bio-compatible material, e.g., titanium, encapsulates at least a portion of the implantable device, including a portion of the input/output device. The encapsulating layer encapsulates substantially all surfaces of the implantable device that are not biocompatible. At least one bio-compatible electrical contact of the input/output device is exposed through the encapsulating layer. The encapsulating layer and the layer of bio-compatible, hermetic insulator material form a hermetic seal around the at least one exposed bio-compatible electrical contact.

In one implementation, the input/output device is configured to generate, transmit, receive, and/or process electrical signals associated with an implant sight. The input/output device may include a thinned die. The die may be thinned, for example, such that a surface of the input/output device is coplanar with a surface of the substrate.

The insulator layer may include, in various implementations, diamond, ruby, ceramic, parylene, sapphire, alumina, glass, or a combination thereof. The insulating layer, in some implementations is electrically insulating.

In some implementations, the implantable device includes a second device coupled in a second recess formed in the substrate. An interconnect encapsulated within the encapsulating layer electrically and communicatively couples the input/output device to the second device. In addition, or in the alternative, the implantable device may include an antenna and/or an inductive coil either encapsulated within the encapsulating layer or coupled to the input/output device outside of the encapsulating layer.

The methods disclosed herein include a method for manufacturing an implantable bio-compatible integrated circuit device. A substrate having a recess is provided, and a input/output device comprising at least one bio-compatible electrical contact is coupled to the substrate in the recess. A bio-compatible, hermetic insulator is applied to a portion of the input/output device, using, for example, a PECVD, LPCVD, or a similar process. At least a portion of the implantable device, including a portion of the input/output device, is encapsulated with an encapsulating layer of bio-compatible material, e.g., by depositing the encapsulating material using a sputtering or atomic layer deposition process. At least one bio-compatible electrical contact of the input/output device is exposed through the encapsulating layer, such that a hermetic seal is preserved between the encapsulating layer and the layer of bio-compatible, hermetic insulator material around the at least one exposed bio-compatible electrical contact.

In some implementations, additional input/output devices are coupled to other recess in the substrate. After application of the encapsulating layer, the substrate is singulated to yield multiple separate bio-compatible implantable devices.

In certain implementations, the method includes coupling a second device into a second recess in the substrate and electrically and communicatively coupling the second device to the input/output device prior to encapsulating portions of the implantable device.

DETAILED DESCRIPTION

To provide an overall understanding of the invention, certain illustrative embodiments will now be described, including a bio-compatible hermetic iUHD device, which facilitates the ultra miniaturization of implantable medical devices. However, it will be understood by one of ordinary skill in the art that the systems and methods described herein may be adapted and modified as is appropriate for the application being addressed and that the systems and methods described herein may be employed in other suitable applications, and that such other additions and modifications will not depart from the scope thereof.

Figure 1A:
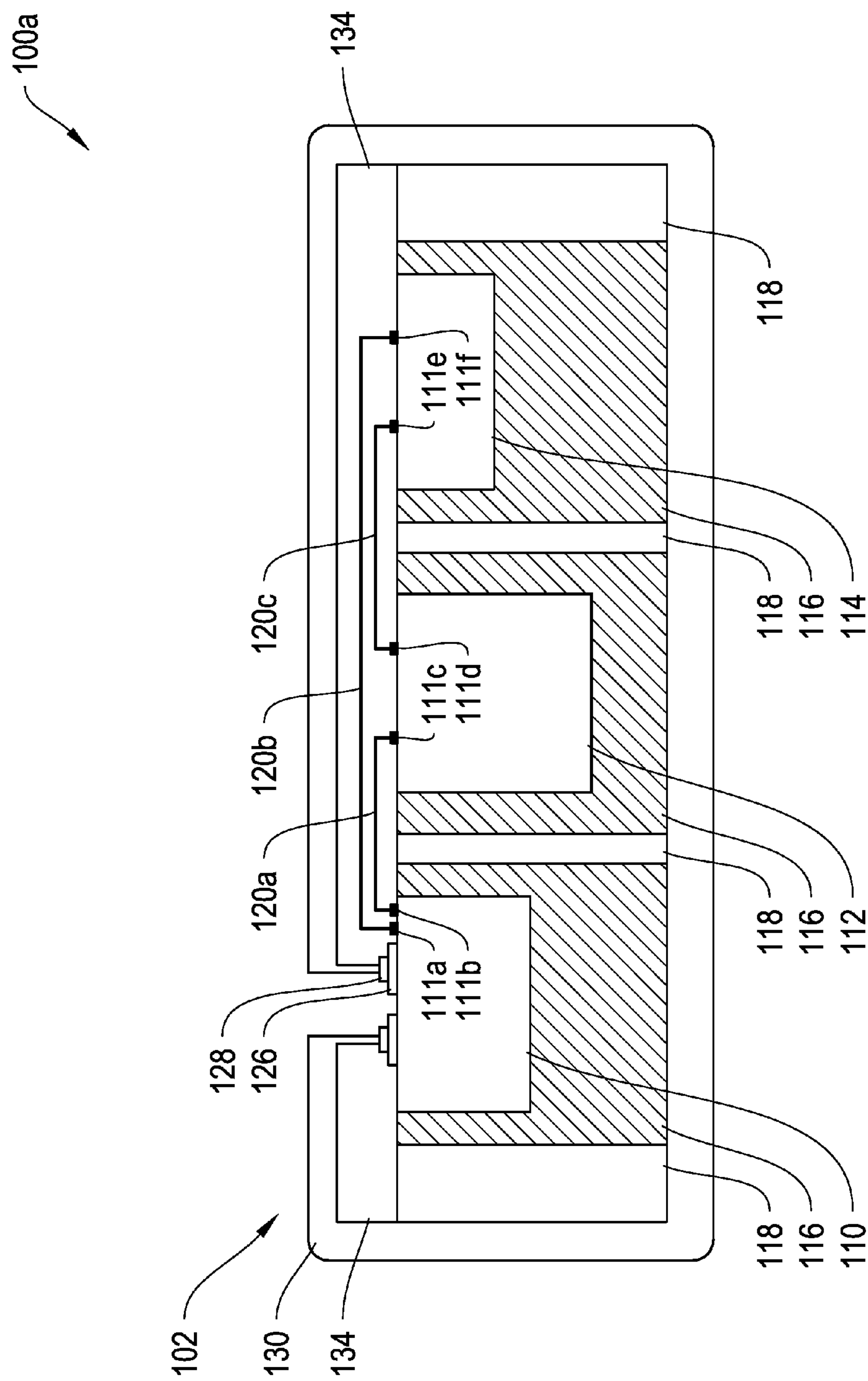
FIG. 1A is a cross-sectional view of a bio-implantable hermetic iUHD device, according to an illustrative embodiment of the invention.
Figure 1B:
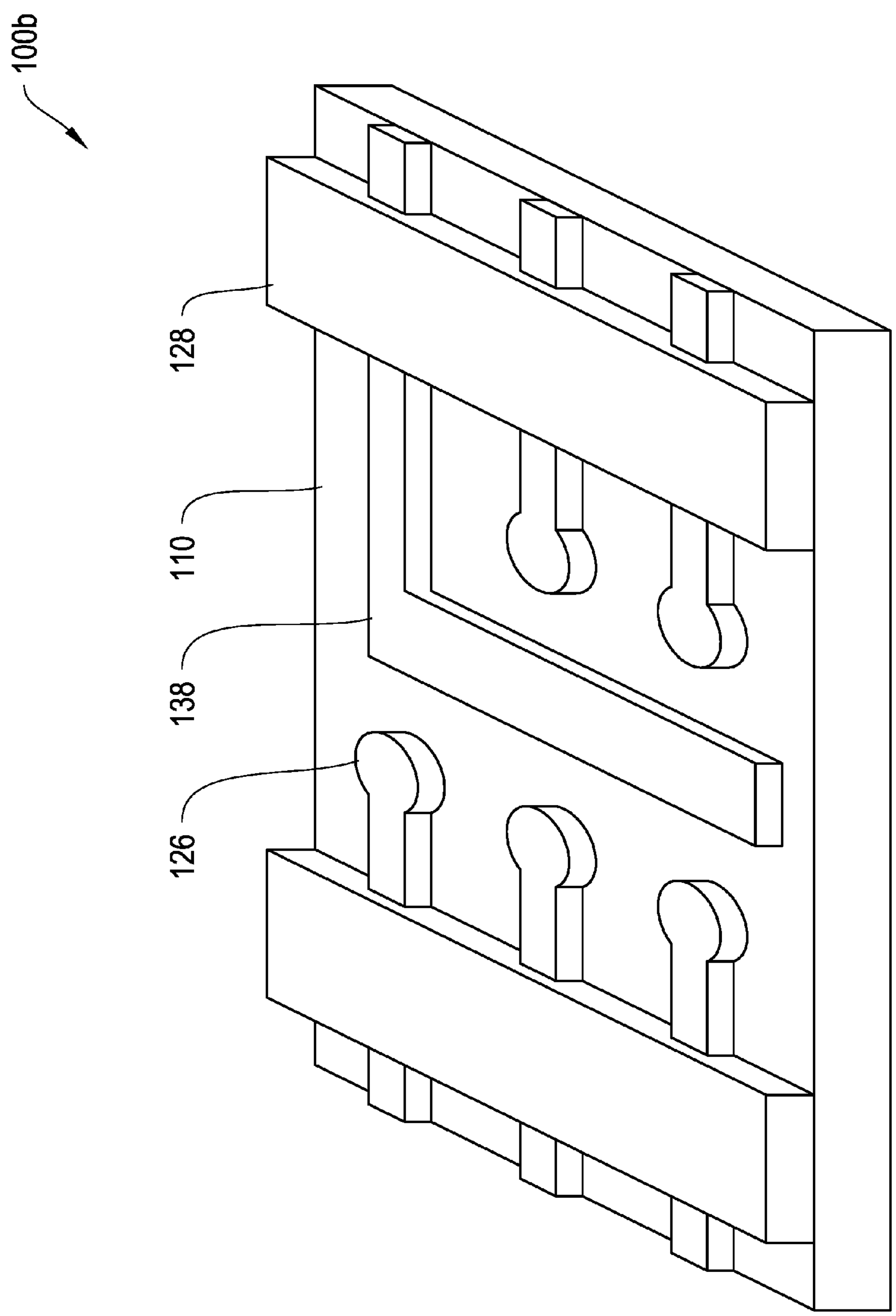
FIG. 1B is a perspective view of a portion of a front surface of a bio-implantable hermetic iUHD device, according to an illustrative embodiment of the invention.
Figure 1C:
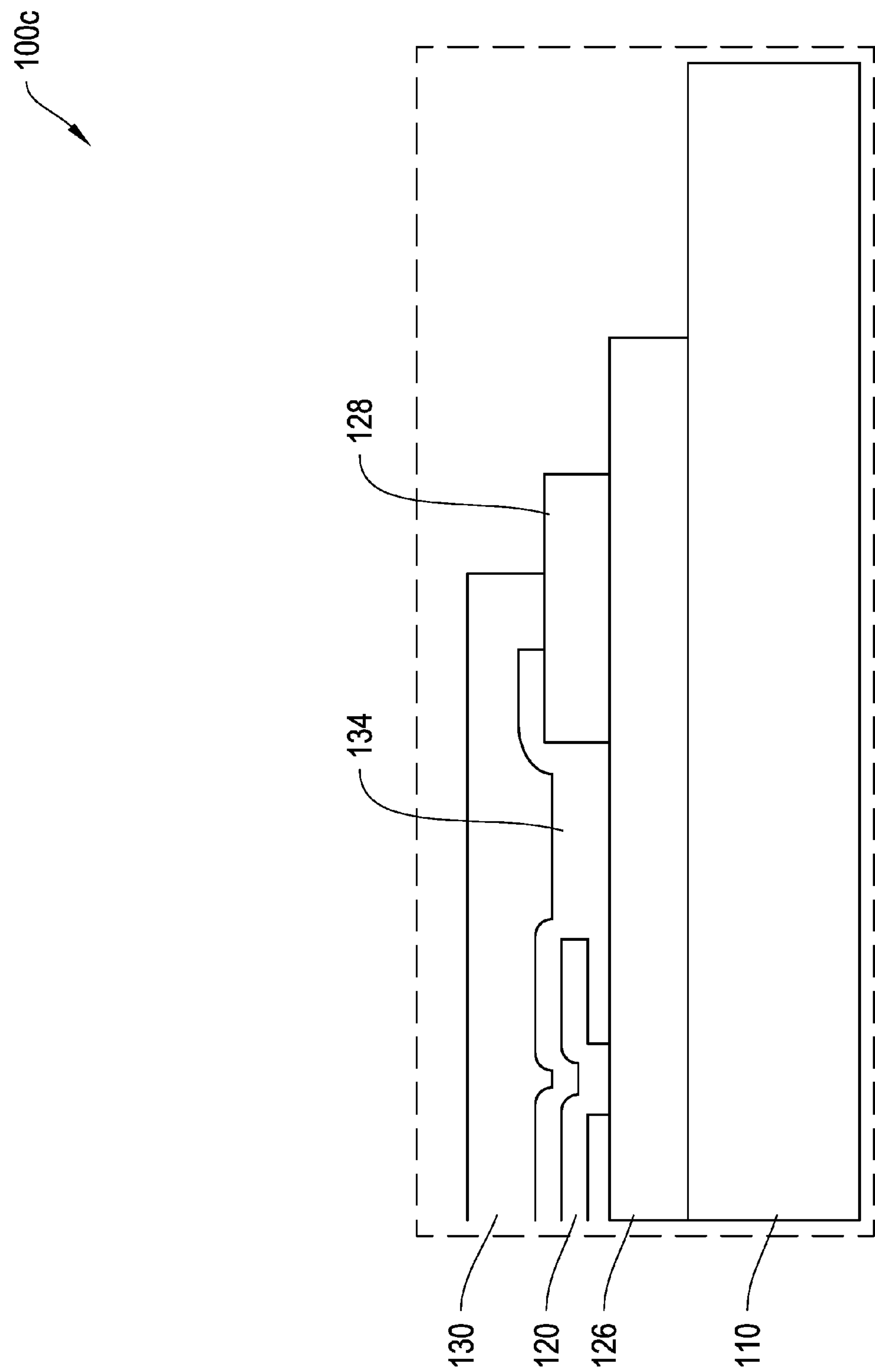
FIG. 1C is a close-up cross-sectional view of a portion of a bio-implantable hermetic iUHD device, according to an illustrative embodiment of the invention.

FIGS. 1A-1C depict various views of a bio-implantable hermetic iUHD device 102, or portions thereof, according to an illustrated embodiment of the invention. FIG. 1A is a cross-sectional view 100*a* of the bio-implantable hermetic iUHD device 102. FIG. 1B is a perspective view 100*b* of a portion of a front surface of the bio-implantable hermetic iUHD device. FIG. 1C is a close-up cross-sectional view 100*c* of a portion of the bio-implantable hermetic iUHD device similar to the portion depicted in FIG. 1B.

Now referring to FIGS. 1A-1C, bio-implantable hermetic iUHD device 102 includes two integrated circuit (IC) devices 112 and 114 and a third chip I/O chip 110 with biocompatible electronic feed throughs and possibly ICs, embedded in a substrate 118 and an encapsulating layer 130. The substrate 118 is rigid and is formed from a material such as glass, ceramic, or silicon (Si). Three recesses (or cavities) have been formed into the substrate 118 for housing the three IC devices. The IC devices 110, 112, and 114 may, but need not be, iUHD devices, which are high-density electronic modules that include dies that may have been thinned to take up substantially less volume than conventional electronic modules. U.S. Pat. No. 8,017,451, U.S. patent application Ser. No. 13/222,764, and U.S. patent application Ser. No. 12/407,252 describe various iUHD devices and methods for their manufacture in detail and are hereby incorporated herein by reference.

IC devices 110, 112, and 114 have different heights and shapes, and the dimensions of a recess are sized appropriately to fit each IC device. Insulating material 116, e.g. potting compound dielectric material such as silicon dioxide or any suitable dielectric material commonly used in the semiconductor industry, surrounds each IC device to maintain its position relative to the substrate and to fill in the extra space remaining in the corresponding recesses. The top portions of the IC devices are coplanar at the top edge of the substrate 118. Dimensions of the substrate and/or IC devices vary approximately between 1 mm and 40 mm on a side. In FIG. 1A, the recesses penetrate through the entire thickness of the substrate 118. However, the recesses may also penetrate only a portion of the thickness of the substrate, and it will be understood by one of ordinary skill in the art that the recesses may take any suitable shape and size to adequately support a position of an IC device.

IC devices 110, 112, and 114 are configured to receive, process, generate, and/or transmit electrical signals. For example, an IC device may include a packaged assembly of multiple devices (e.g., a hermetically packaged sensor and/or microelectromechanical systems (MEMS) device), a microcontroller, a central processing unit, or another type of chip utilized in various electronic components such as sensors or computers. The signals may be physiological signals recorded at a site in a biological system and transmitted to the device 102 for processing. Alternatively, the signals may be generated by the device 102 and transmitted to a site in a biological system for stimulation or signals originating from or transmitted to a device external to the body, e.g., a medical monitoring device.

The device 102 is designed to be implanted inside a biological system such that all exposed portions of the device 102 are bio-compatible. The entire device 102 (with the exception of a top portion of the I/O chip 110) is encapsulated by a hermetically sealed encapsulating layer 130 made of a bio-compatible material such as titanium (Ti), ceramics, metals, polymers or other material commonly used for housing implantable devices. In general, any exposed portion of the device 102 or any implantable device described herein is formed from or coated with a bio-compatible material.

The perspective view 100*b* of FIG. 1B shows a top portion of the I/O chip 110 in the device 102 shown in FIG. 1A. As shown in FIG. 1B, a top portion of the I/O chip 110 is exposed to the external environment, and the exposed front surface of the I/O chip 110 is formed from or coated with a bio-compatible material. IC devices 112 and 114 are fully encapsulated by the encapsulating layer 130, meaning that, in contrast to I/O chip 110, no portions of the IC devices 112 and 114 are exposed to the external biological environment.

I/O chip 110 is an input/output (I/O) IC device that provides communication between the device 102 and the surrounding biological system and/or devices external to the biological system by receiving and transmitting electrical signals. The substrate of the I/O chip 110 is either itself biocompatible, or exposed surfaces of the substrate are coated with a biocompatible material. In FIG. 1B, five terminals 126 are exposed to the external environment and are made of a bio-compatible conductive material such as platinum (Pt), gold (Au), Ti, an alloy thereof, or any other suitable bio-compatible conductive material commonly used in implantable medical devices. The terminals 126 are hermetically sealed between the top of the I/O chip 110 and a layer of bio-compatible, hermetic insulator 128. The hermetic seal ensures that molecules (including solids, liquids, and gases) are unable to permeate between the biological environment and the interior of device 102. The bio-compatible, hermetic insulator 128 includes dielectric material such as diamond, ruby, ceramic, parylene, sapphire, alumina, glass, and may be deposited using a plasma enhanced chemical vapor deposition (PECVD) or low-pressure chemical vapor deposition or a similar process.

Interconnects 120*a*-120*c* (generally interconnects 120) electrically and communicatively couple two or more IC devices to each other by forming connections between terminals 111*a*-111*f* (generally terminals 111) at the top of the IC devices. The interconnects 120 and terminals 111 include conductive material such as copper (Cu) or any suitable conductive material commonly used in the semiconductor industry. Alternatively, some or all of the interconnects 120 are formed from optical waveguides and other optical components to facilitate optical communication across IC devices. In FIGS. 1A and 1*n* the close-up cross-sectional view 100*c* of FIG. 1C, dielectric material 134 separates the conductive material and provides insulation between the interconnects 120. The materials included in the interconnects 120, terminals 111, and dielectric material 134 do not have to be biocompatible, because, as was described above, the device 102 is encapsulated by a hermetically sealed bio-compatible material 130.

In some embodiments, a bio-compatible encapsulating layer 130 on a surface or a portion of a surface of device 102 is not required if the exposed portion of the device 102 includes bio-compatible material. For example, substrate 118 may be formed from bio-compatible material such that the side walls of the encapsulating layer 130 shown in FIG. 1A are not necessary. Similarly, if the insulating material 116 also is formed from bio-compatible material, the back surface of the device 102 may not require a bottom encapsulating layer 130.

In some embodiments, additional devices are included in the device 102. In this case, additional recesses are formed to house these devices, and additional interconnects provide electrical and communicative coupling across the different devices. For example, additional IC devices may be configured to further process the received signals and/or the generated signals. In another example, a power supply such as a thin film battery that supplies power to the device 102 may be coupled to the substrate in a recess. In another example, the device 102 may be powered using inductive coils that provide electromagnetic power or communication. In some embodiments, only one or two IC devices are included in the device 102. If the I/O chip 110 is the only IC device in the device 102, the I/O chip 110 performs a combination of receiving, processing, generating, and/or transmitting of signals. It will be understood to one of ordinary skill in the art that any number of IC devices may be included in the device 102.

In some embodiments, the device 102 is a monitoring device that only receives signals from the surrounding tissue, e.g. heart monitor, and the device does not transmit signals for stimulation. In other embodiments, the device 102 only transmits signals to the surrounding tissue for stimulation or to one or more external devices, and the device does not receive signals. In other embodiments, the device 102 performs both functions of receiving and transmitting signals at a site in a biological system or one or more external devices.

In some embodiments, device 102 includes an antenna 138 as depicted in FIG. 1B. The antenna 138 extends across a portion of the exposed front surface of the I/O chip 110. The antenna 138 is configured to receive and transmit wireless signals and allows for wireless communication between the device 102 and an external device. Reducing the use of wires in some medical implants allows for even greater freedom in selecting where the device 102 is placed in the body. For example, it may be desirable to place an electrical contact in a certain location, but placing wires near the location would pose significant risks. In this case, using wireless signals to transmit and receive data would be beneficial. In other embodiments, the device 102 does not include an antenna, and all communication between the device 102 and the biological environment occurs over wired connections connected to terminals 126.

In some embodiments, the I/O chip 110 is a simple substrate without any logic circuitry, as depicted in FIG. 1C. That is, the I/O chip 110 in this case is intended merely as an access port to the external environment. In this case, terminals 126 are formed on the surface of the substrate of the I/O chip 110 and are directly electrically and communicatively coupled to interconnects 120 leading to other devices. In other embodiments, the I/O chip 110 includes circuitry to process the received and/or transmitted signals. For example, the I/O chip 110 may modulate a signal at an appropriate carrier frequency before outputting the signal to the antenna 138 or demodulate received signals from other devices to extract data or instructions.

Figure 2A:
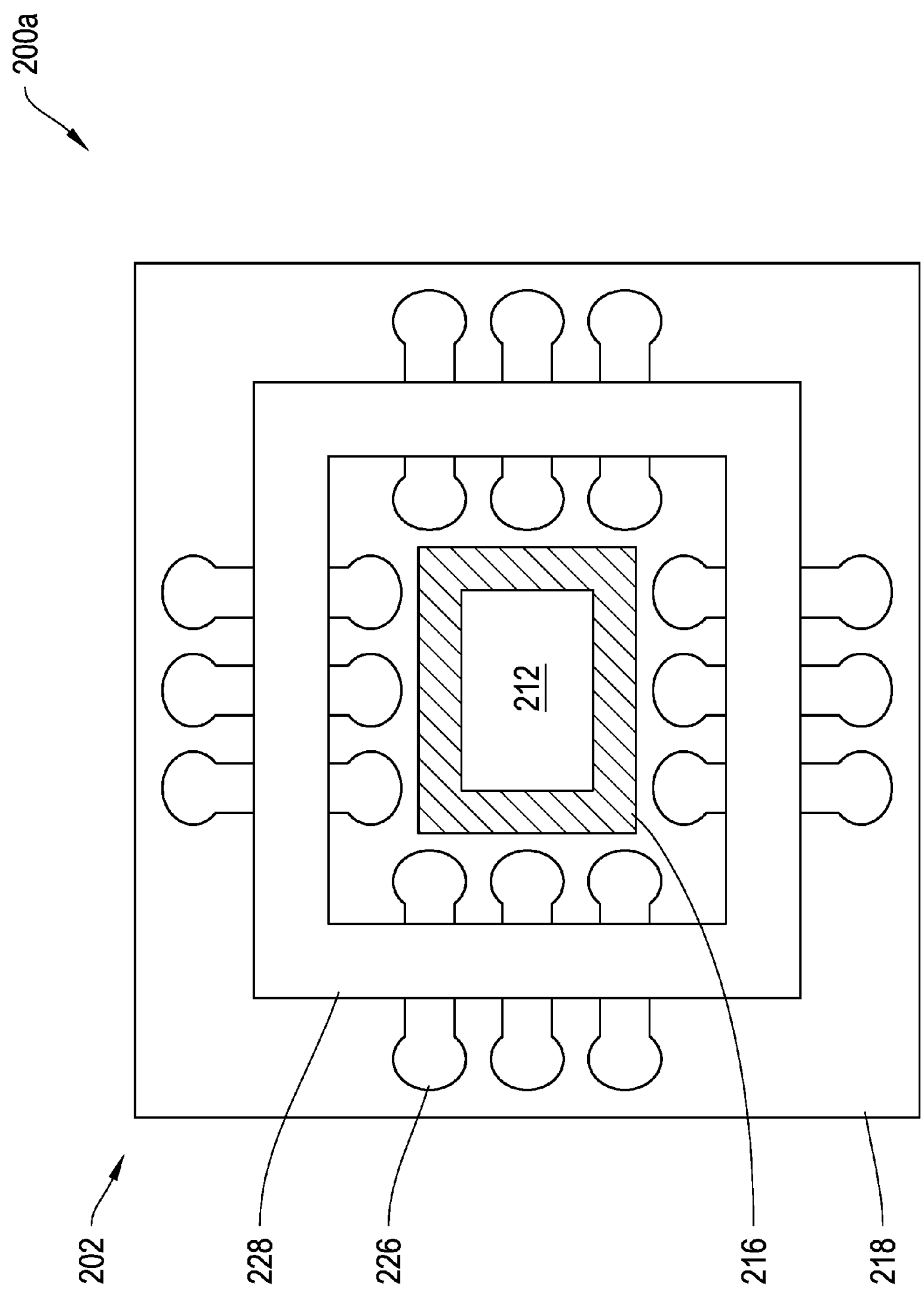
FIG. 2A is a perspective view of a front surface of a bio-implantable hermetic iUHD device, according to an illustrative embodiment of the invention.
Figure 2B:
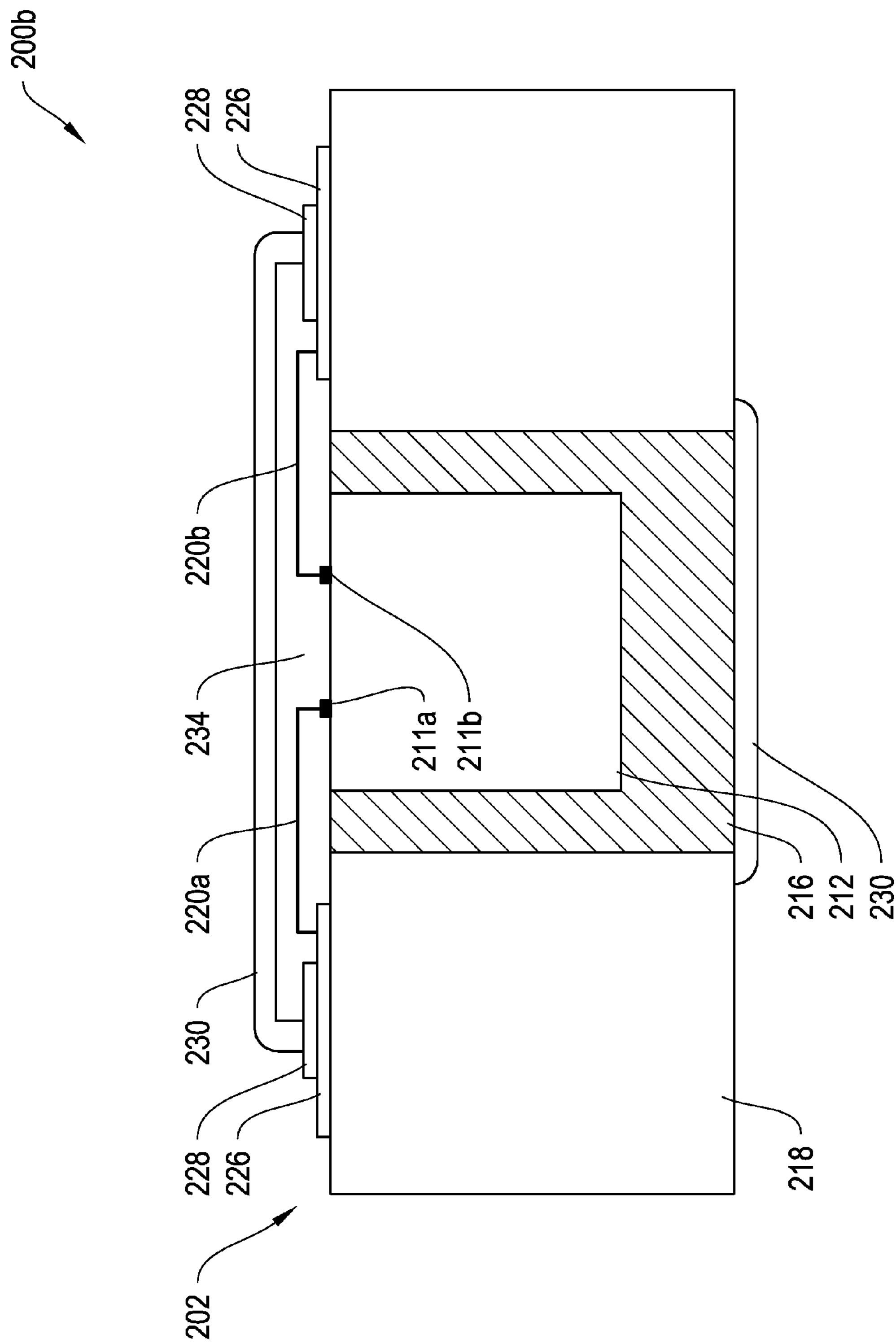
FIG. 2B is a cross-sectional view of a bio-implantable hermetic iUHD device, according to an illustrative embodiment of the invention.

FIGS. 2A and 2B are top down and cross-sectional views, respectively, of an alternative implementation suitable for a portion of a bio-implantable hermetic iUHD device. Now referring to FIGS. 2A-2B, a portion of the bio-implantable hermetic iUHD device 202 includes an IC device 212 surrounded by insulating material 216 and substrate 218. In this configuration, terminals 226 are formed at the perimeter of the front surface of the substrate 218 and are hermetically sealed between the substrate 218 and a layer of bio-compatible, hermetic insulator 228. For clarity, interconnects forming connections between terminals 226 and IC device 212, layers of dielectric material, and the encapsulating layer of bio-compatible material are not shown in diagram 200*a*. These components are displayed in the cross-sectional view of diagram 200*b*. Interconnects 220*a* and 220*b* electrically and communicatively couple two terminals 226 to terminals 211*a* and 211*b* on the front surface of IC device 212. Dielectric material 234 provides insulation between the interconnects 220 and other front surface materials, and encapsulating layers 230 cover portions of the device 202 with bio-compatible material. The device 202 includes a substrate 218 made of bio-compatible material (e.g., silicon), such that an encapsulating layer 230 is not required to encapsulate the remainder of the substrate.

In some embodiments, dielectric material 234 is bio-compatible, such that the top layer of encapsulating layer 230 in diagram 200*b* is not necessary. Similarly, insulating material 216 may be bio-compatible, precluding the need for the bottom layer of encapsulating layer 230 in diagram 200*b*. Alternatively, dielectric material 234, insulating material 216, and substrate 218 may not include bio-compatible materials, thereby requiring an encapsulating layer surrounding these portions of the device 202.

Figure 2C:
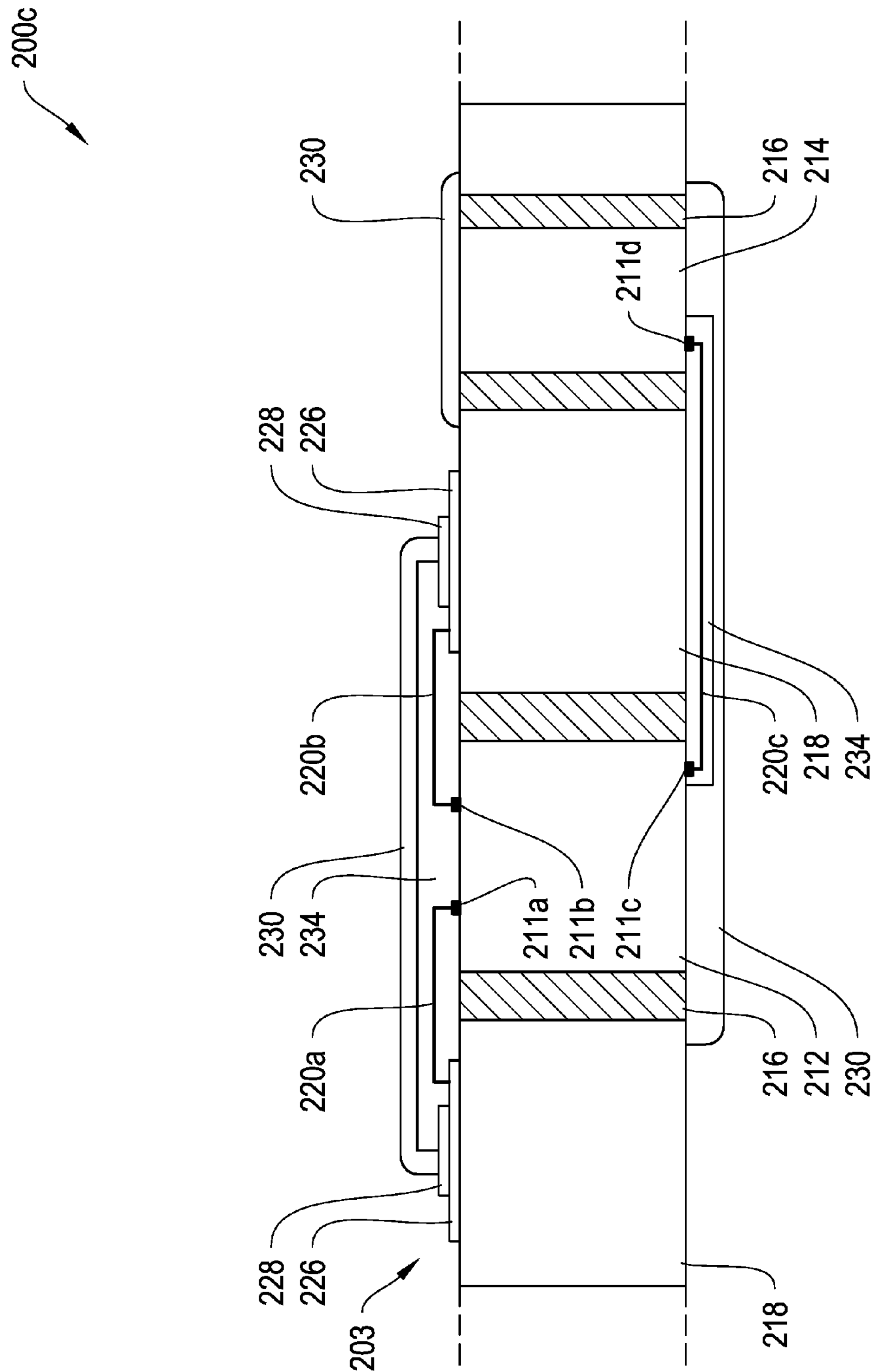
FIG. 2C is a cross-sectional view of an alternative I/O chip implementation suitable for use in the iUHD device of FIG. 1.
Figure 3A:
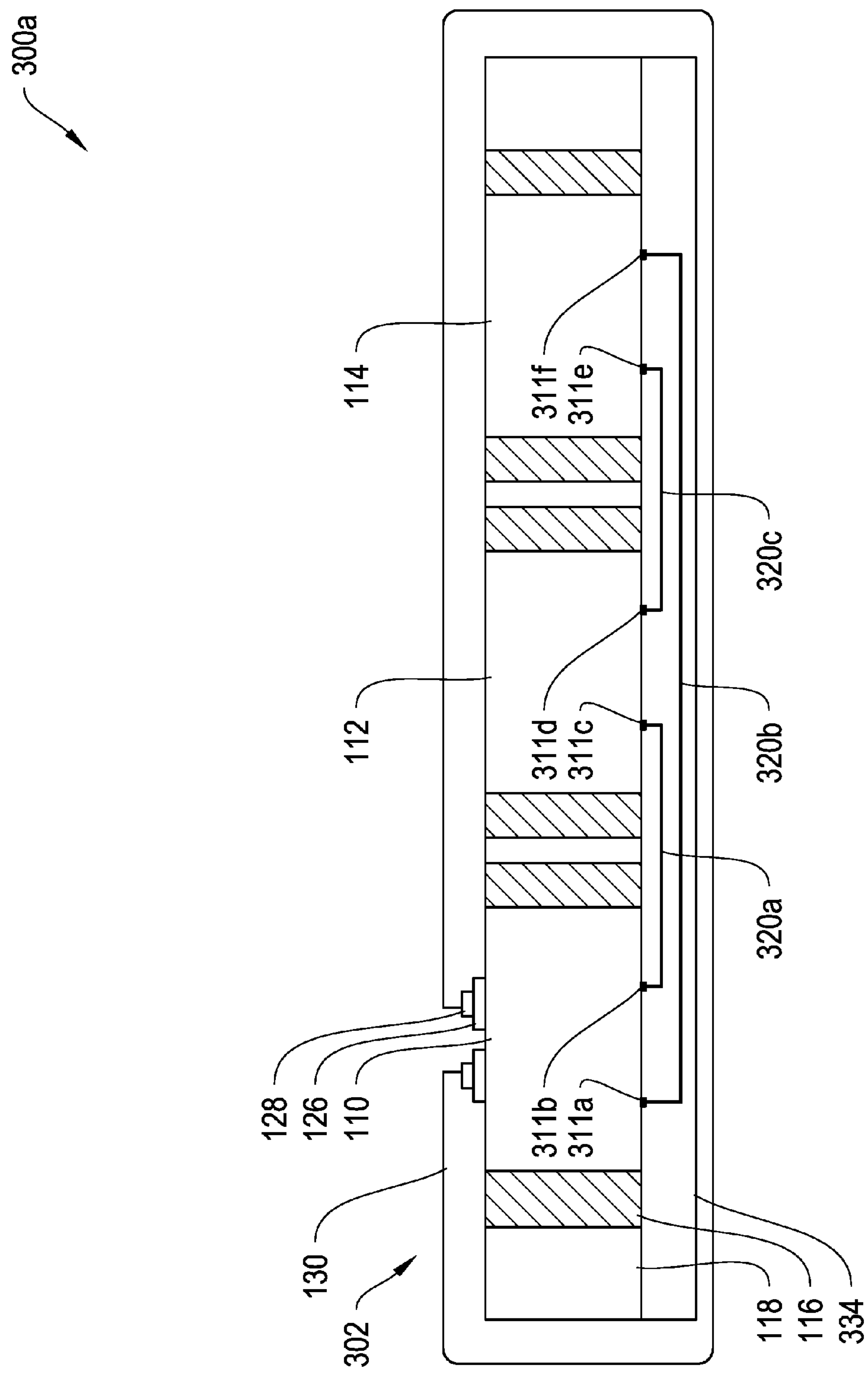
FIGS. 3A and 3B are cross-sectional views of a bio-implantable hermetic iUHD device, according to illustrative embodiments of the invention.
Figure 3B:
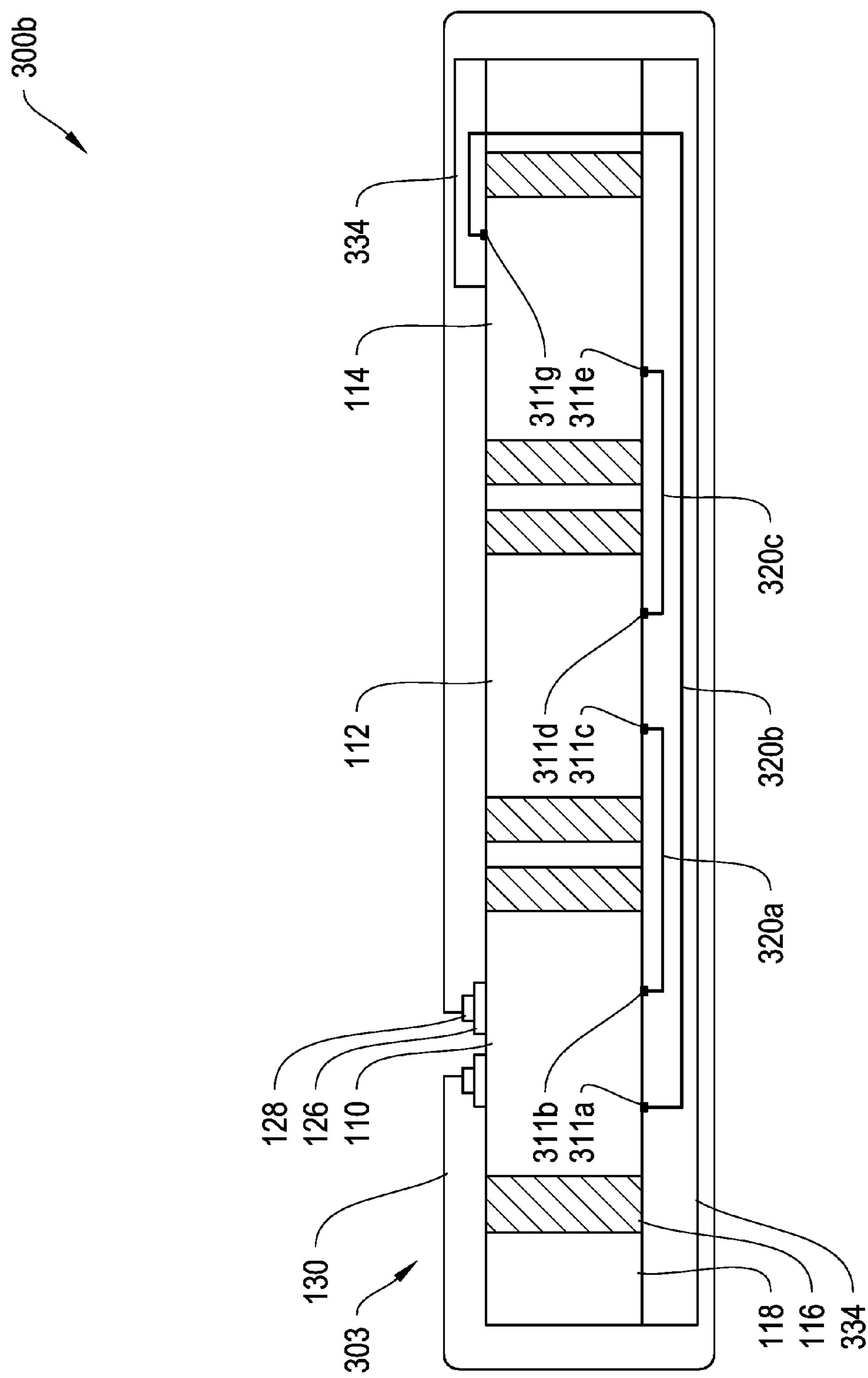

FIG. 2C is a cross-sectional view of an alternative I/O chip implementation suitable for use in the iUHD device of FIG. 1. The components of device 203 include the same components as in device 202, except that the device 203 includes an additional IC device 214, which is coupled to the IC device 212 over an interconnect 220*c* formed at the back surface of the device 203. The interconnect 220*c* is insulated by layers of dielectric material 234. In order to facilitate the formation of interconnects at the back surface of the device 203, the IC devices 212 and 214 included in the device 203 are selected to have the same depth as the I/O chip 210. In addition, after the I/O chip 210 and IC devices 212 and 214 are coupled to the device 203, the back surface of the substrate 218 is thinned such that it is co-planar with terminals of the I/O chip 210 and the IC devices 212 and 214. Alternatively, the dies of the I/O chip 210 and/or IC devices 212 and 214 may be thinned to such that they have substantially the same depth or thickness as the substrate 218 and I/O chip 110. Additional IC devices may also be included in device to the left and/or right of the diagram 200*c* or into or out of the plane of FIG. 2C FIGS. 3A-3B are cross-sectional views of alternative bio-implantable hermetic iUHD device implementations. Device 302 in FIG. 3A is similar to device 102 in FIG. 1A, with the exception that instead of having terminals 111 positioned at the front surfaces of the IC devices 110, 112, and 114, the terminals 311*a*-311*f* are positioned at the back surfaces of the IC devices. Furthermore, instead of having interconnects 120 positioned at the top of the device, interconnects 320 are positioned near the back surface of the device 302. The dielectric material 334 that provides insulation between interconnects 320 is also positioned near the back surface of the device 302.

In order to facilitate the formation of interconnects at the back surface of the device 302, the IC devices 112 and 114 included in the device 302 are selected to have the same depth as the I/O chip 110. In addition, after the I/O chip 110 and IC devices 112 and 114 are coupled to the device 302, the back surface of the substrate 118 is thinned such that it is co-planar with terminals of the I/O chip 110 and the IC devices 112 and 114. Alternatively, the dies of the I/O chip 110 and/or IC devices 112 and 114 may be thinned to such that they have substantially the same depth or thickness as the substrate 118. Additional IC devices may also be included in device to the left and/or right of the diagram 300*a* or into or out of the plane of diagram 300*a*.

Device 303 in FIG. 3B is similar to device 302, with the exception that a terminal 311*g* (positioned at the front surface of IC device 114) is substituted for terminal 311*f*. Interconnect 320*b* forms a connection between the IC devices 110 and 114 over a via that passes through a via hole formed in the substrate 118. Dielectric material 134 provides insulation to the interconnects below and above the substrate. Such implementations allow for more complex interconnect structures by allowing interconnects to span across different surfaces of the device 303.

Figure 4A:
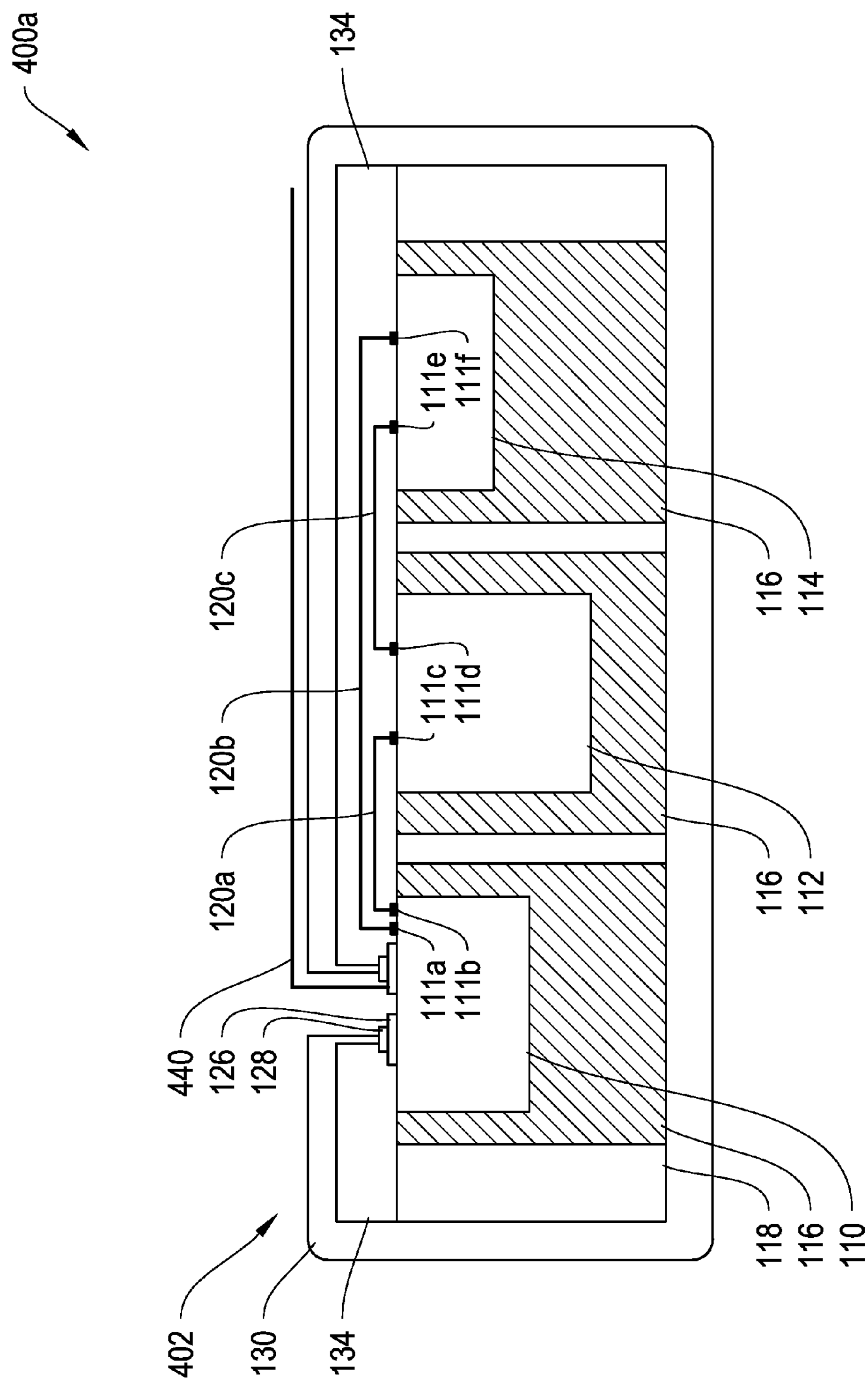
FIGS. 4A-4D are cross-sectional views of additional examples of illustrative bio-implantable hermetic iUHD devices, according to illustrative embodiments of the invention.
Figure 4B:
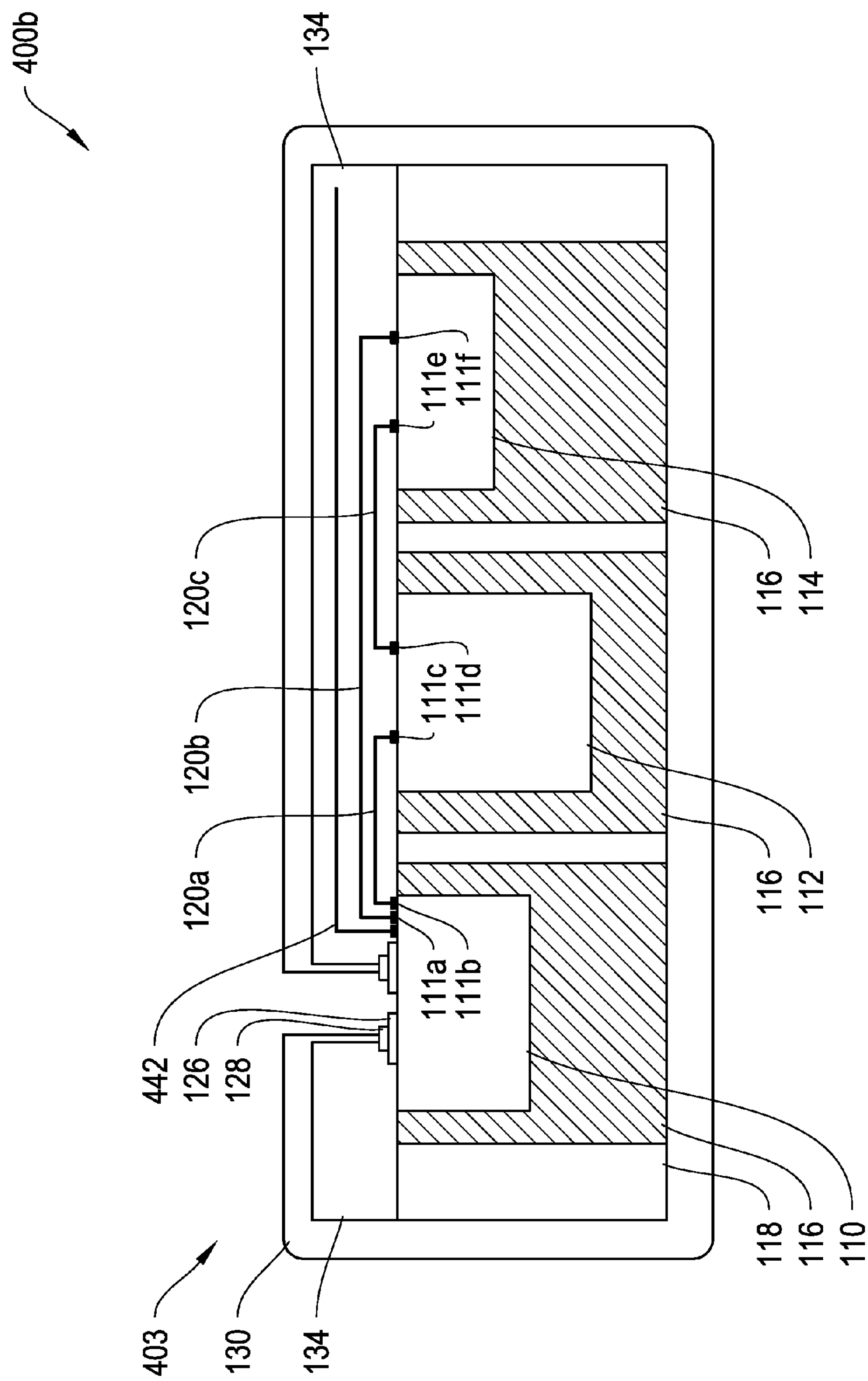

FIGS. 4A-4D are cross-sectional views of additional examples of illustrative bio-compatible, implantable hermetic iUHD devices. Device 402 in FIG. 4A is identical to device 102, with the exception that device 402 includes an alternative antenna 440. The antenna 440 is configured to receive and transmit wireless signals and performs the same functions as antenna 138 as described in relation to FIG. 1B. However, rather than extending over a portion of the exposed surface of the I/O chip 110, antenna 440 extends over the front surface of the device 402. One or both antenna configurations may be included in the device. Because antenna 440 is external to the bio-compatible encapsulating layer 130, antenna 440 is formed from or coated with bio-compatible material. Antenna 440 may be fabricated separately from the device 402 and coupled to the device 402 after the remainder of the manufacture of the device is complete. Device 403 in FIG. 4B is identical to device 402, with the exception that instead of an antenna 440 external to the device, antenna 442 is internal to the device 403 and is insulated by dielectric material 134. In contrast to antenna 440, antenna 442 is fabricated during the fabrication process of the device 403.

Figure 4C:
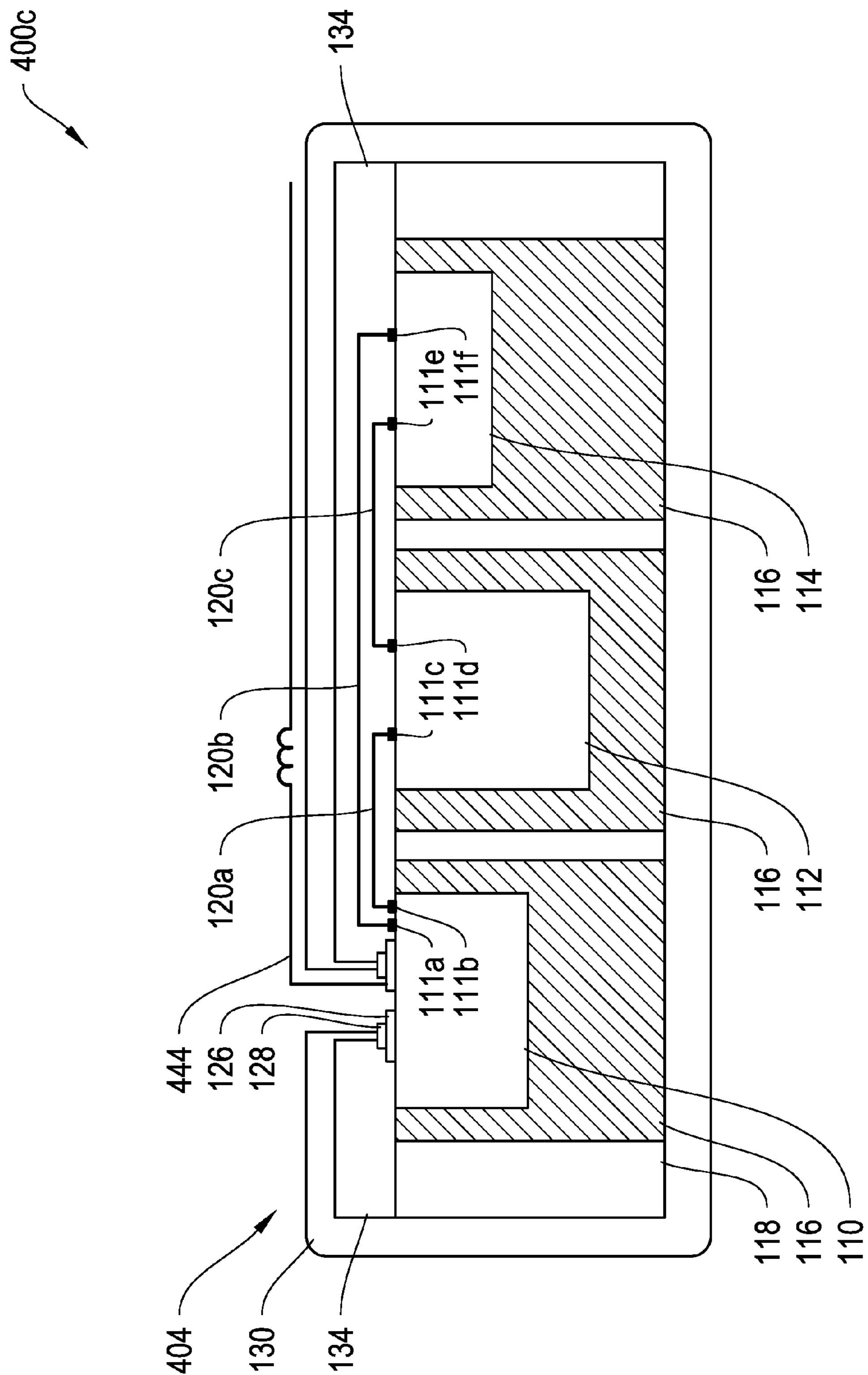
Figure 4D:
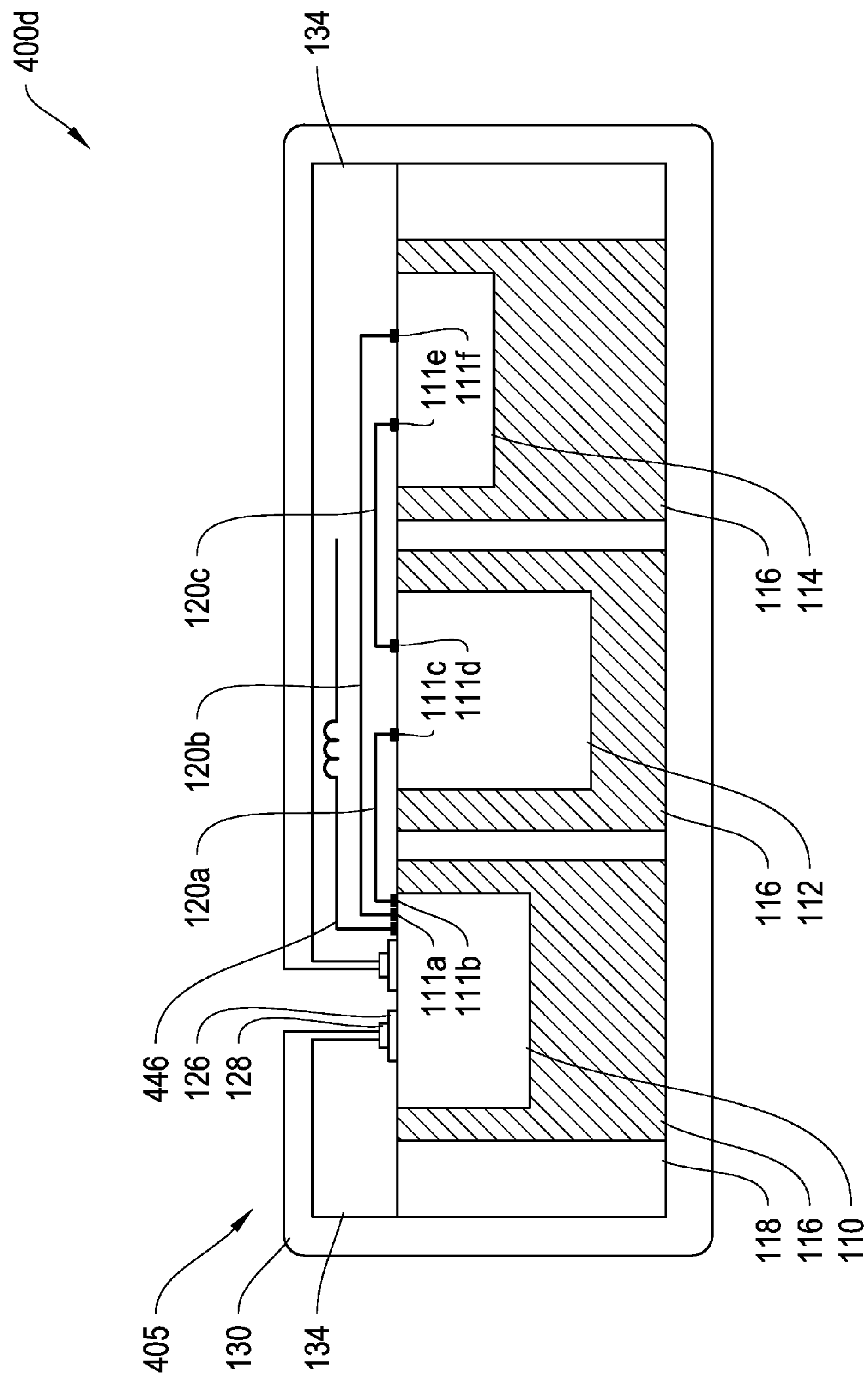

Device 404 in FIG. 4C is identical to device 402, with the exception that instead of an antenna 440, an inductive coil 444 extends over a portion of the front surface of the device 404. The inductive coil 444, in the presence of an appropriate external electromagnetic field, generates a current to charge an energy storage device, such as a thin-film battery or capacitor, in the device via inductive coupling. Device 405 in FIG. 4D is identical to device 404, with the exception that instead of an inductive coil 444 external to the device, an inductive coil 446 is internal to the device and is insulated by dielectric material 134. The inductive coil 446 performs the same functions as the inductive coil 444 and is fabricated during the fabrication process of the device 405. The encapsulating layer 130 is thin enough to allow penetration of signals into the interior of device 405 such that the operation of inductive coil 446 is not substantially impeded.

Various methods for manufacturing iUHD devices have been disclosed in U.S. Pat. No. 8,017,451, U.S. patent application Ser. No. 13/222,764, and U.S. patent application Ser. No. 12/407,252. These processes can be used to form recesses in the substrate 118, attach IC devices 110, 112, and 114 and dielectric material (e.g., insulating material 116) to the recesses, and form interconnects 120 separated by dielectric material 134. Several additional steps are added to these processes to manufacture the bio-implantable hermetic iUHD device 102 and are described below.

Figure 5:
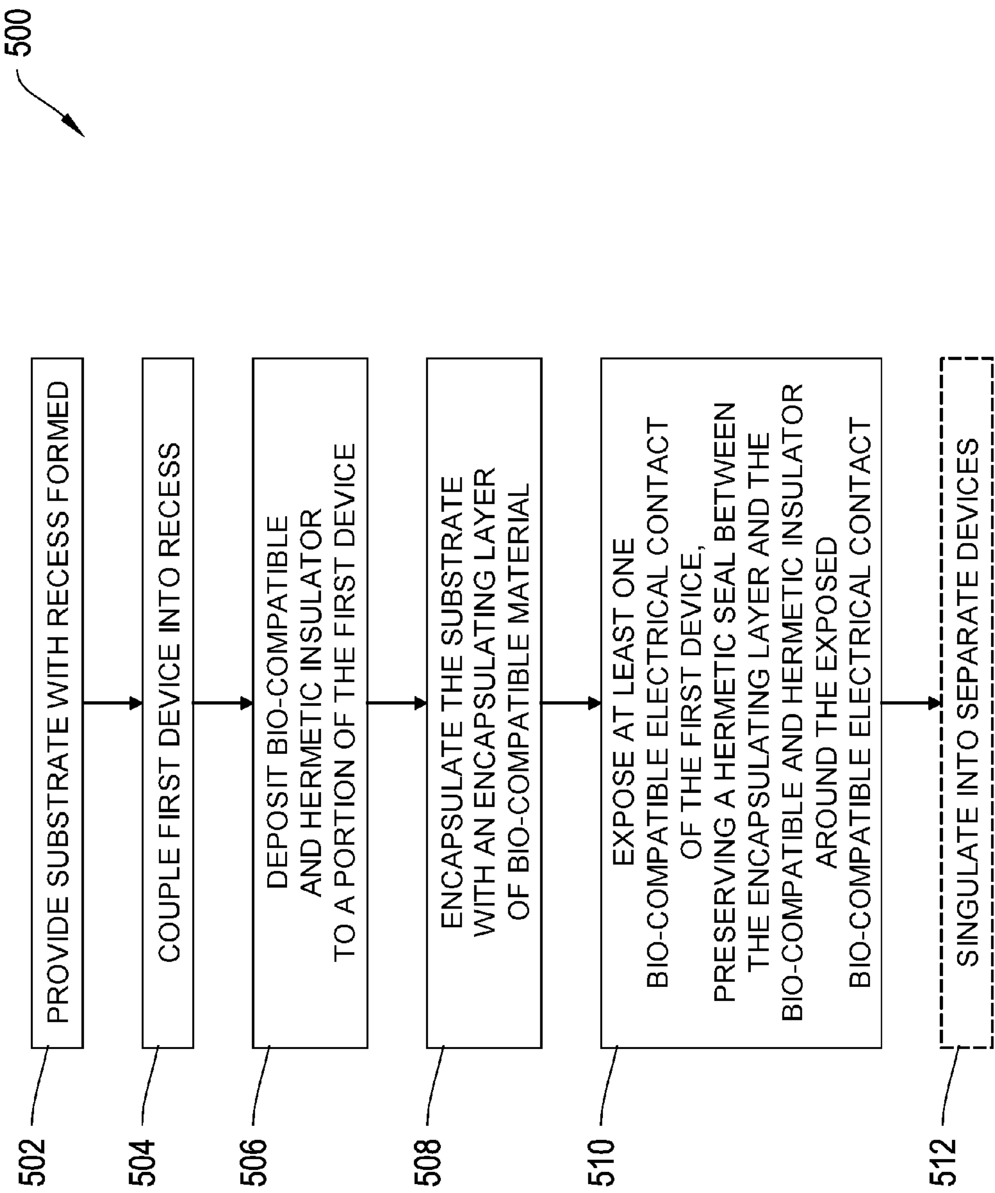
FIG. 5 is a flowchart of a method for manufacturing a bio-implantable hermetic iUHD device, according to an illustrative embodiment of the invention.
Figure 6A:
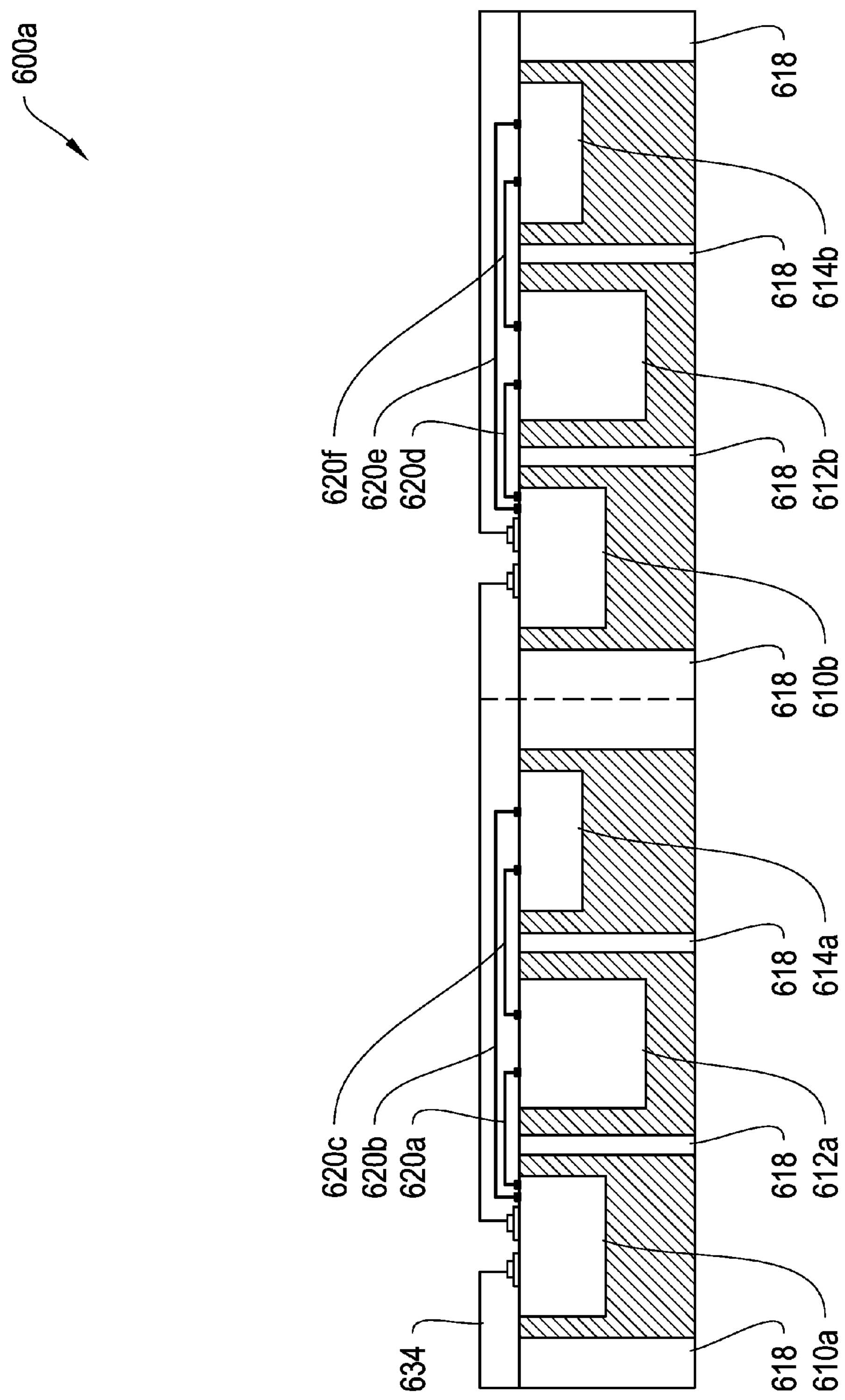
FIGS. 6A-6D are cross-sectional views of two bio-implantable hermetic iUHD devices during a portion of the fabrication process, according to an illustrative embodiment of the invention.
Figure 6B:
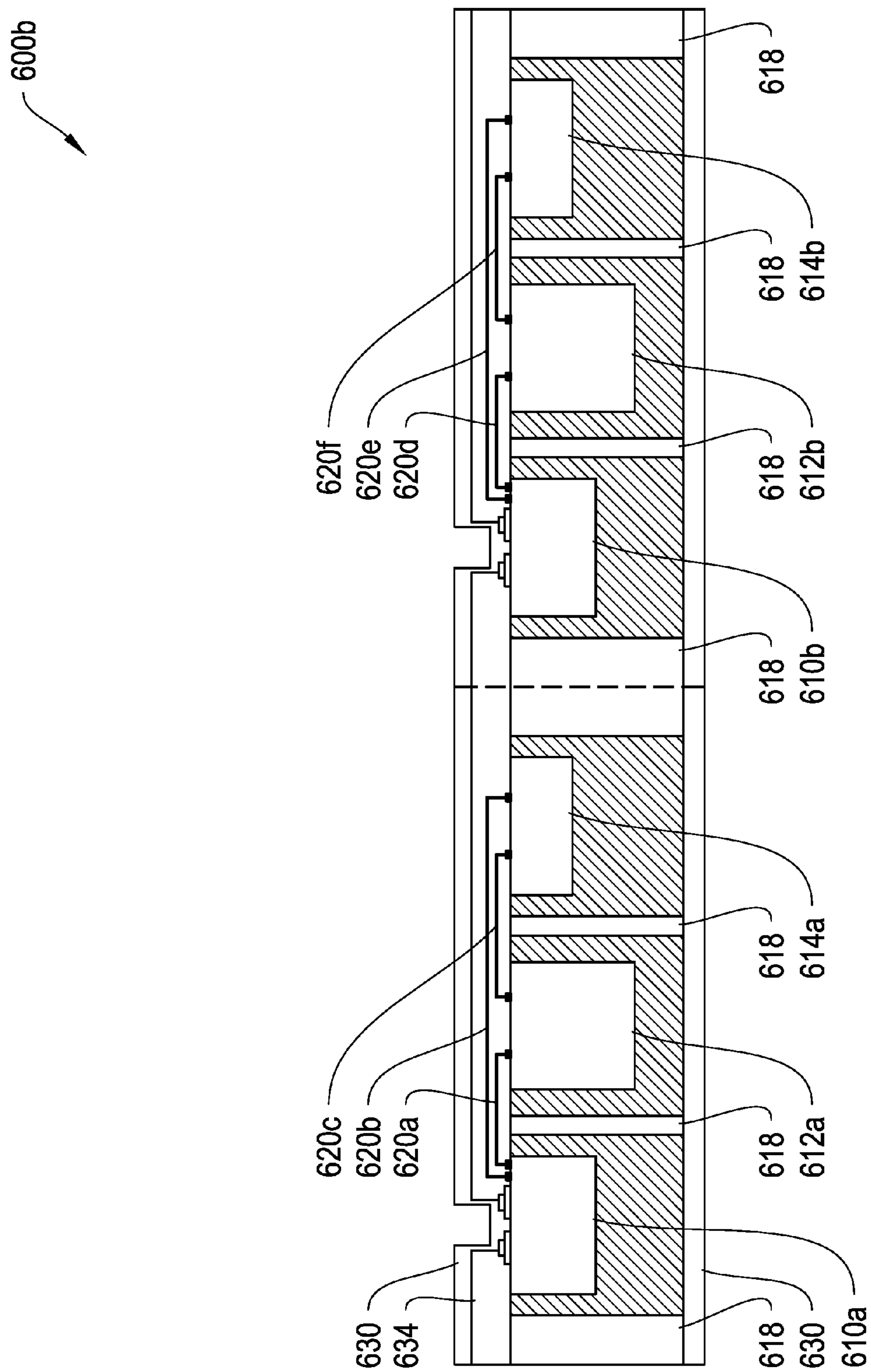
Figure 6C:
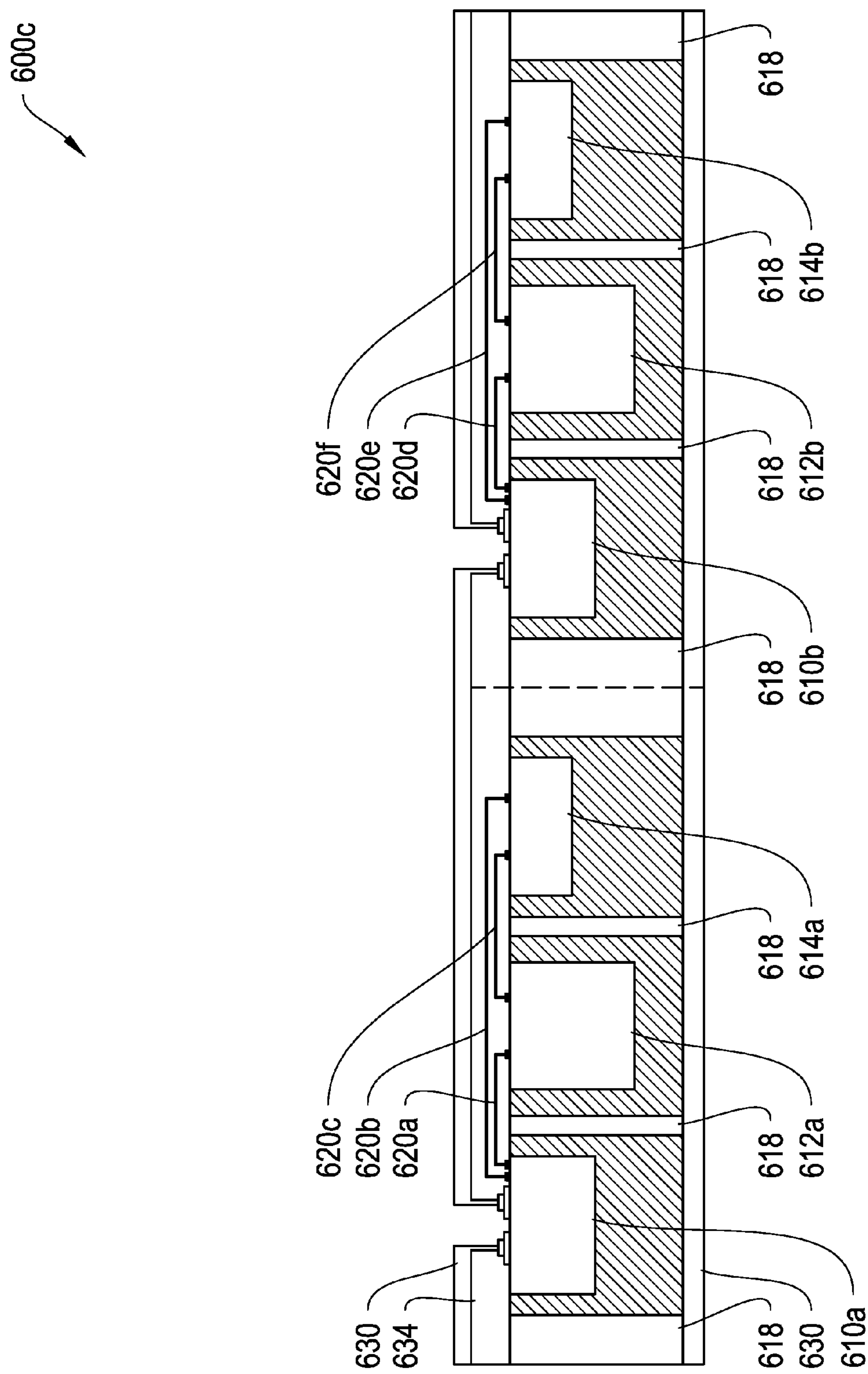
Figure 6D:
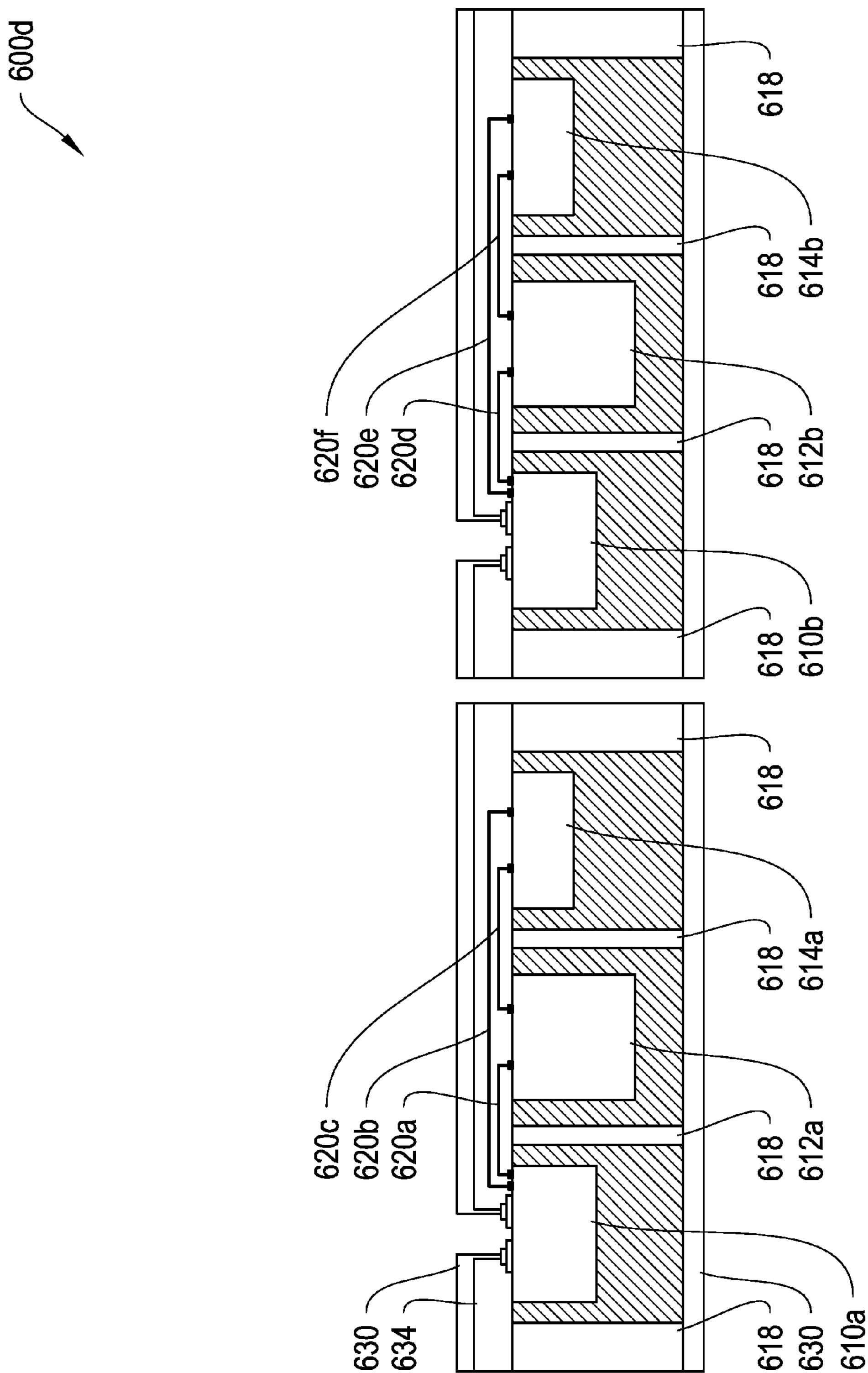

FIG. 5 is a flowchart of a method 500 for manufacturing a bio-compatible, implantable, hermetic iUHD device, according to an illustrative embodiment of the invention. The method 500 includes the steps of providing a substrate with a recess (step 502), coupling a first device into the recess (step 504), depositing a bio-compatible, hermetic insulator to a portion of the first device (step 506), encapsulating the substrate with an encapsulating layer of bio-compatible material (step 508), exposing at least one bio-compatible electrical contact of the first device while preserving a hermetic seal (step 510), and optionally singulating the substrate into separate devices (step 512).

First, a substrate is provided with recesses formed in the substrate (step 502). As described in relation to FIG. 1A, substrate 118 includes a rigid and/or non-conductive material, e.g., glass or a semiconductor such as Si. One or more recesses are formed in the substrate 118 by etching cavities through the thickness of the substrate. Referring now to FIG. 1A, the recesses will eventually contain IC devices such as IC devices 110, 112, or 114. Thus, the recesses are formed such that the shapes and sizes of the recesses are customized to fit the dimensions of the IC devices.

Then, a first device is coupled to the substrate in a recess (step 504). For example, a first device (e.g., I/O chip 110) is temporarily attached to a surface of a temporary substrate. To do this, the I/O chip 110 may be flipped vertically such that the front surface of the I/O chip 110 in the view in FIG. 1A is in contact with a front surface of a temporary substrate. Then, substrate 118 is aligned with the temporary substrate such that the recess is aligned with the I/O chip 110, and such that the surface of the I/O chip 110 (front surface in FIG. 1A) in contact with the temporary substrate is coplanar with a surface of the substrate 118 (front surface in FIG. 1A). Insulating material 116 such as a potting compound is inserted into the remaining portion of the recess. A heat source applies heat to the substrate to cure the insulating material 116 within the recess. This process ensures no air cavities remain between the insulating material 116 and the walls of the recess as well as between the insulating material 116 and the I/O chip 110. Then the insulating material 116 cools and solidifies, thus securely attaching the I/O chip 110 to the substrate 118. The temporary substrate is then removed. This process may be repeated to attach any other IC devices (such as IC devices 112 or 114) to the substrate in additional recesses.

Separate fabrication of the IC devices allows for different manufacturing processes to be used for each IC device. In addition, separate fabrication allows for a greater selection of materials to be used in each IC device.

Then a layer of hermetic bio-compatible insulating material 128 is deposited on a portion of the first device (step 506). The cross-sectional view 100*c* of a portion of the device 102 in FIG. 1C shows a layer of insulating material 128 on top of a terminal 126 of the I/O chip 110. The terminal 126 is hermetically sealed between the insulating material 128 and the I/O chip 110 such that fluids do not penetrate between the biological environment and the device 102.

The substrate 118 is encapsulated in an encapsulating layer 130 of bio-compatible material (step 508). The bio-compatible encapsulating layer includes a bio-compatible material such as Ti and may be deposited on the device by using a thin film deposition technique such as sputtering, atomic layer deposition, or any other technique known for depositing a thin layer of material on surfaces of the device 102. A portion of the I/O chip 110 including at least one bio-compatible electrical contact (i.e., terminals 126) is exposed or patterned while preserving a hermetic seal between the encapsulating layer 130 and the bio-compatible, hermetic insulator 128 around the exposed bio-compatible electrical contact (step 510). For example, the appropriate portion for the I/O chip 110 may be exposed by removal of a portion of the encapsulating layer 130 that was deposited in step 508 using standard etching processes. Alternatively, the portion of the I/O chip 110 desired to be exposed may have been appropriately covered with a covering material when the encapsulating layer 130 was deposited in step 508 such that the desired portion of the I/O chip 110 was never in contact with the encapsulating material. In this case, after encapsulation, the covering material is appropriately removed, exposing a portion of the I/O chip 110 while preserving a hermetic seal.

In some embodiments, multiple IC devices are included in the implantable device, and a first IC device is electrically coupled to a second IC device by forming an interconnect 120 that includes conductive material to provide electrical communication between the two devices. Standard methods of forming interconnects are well known in the semiconductor industry. Briefly, an interconnect is formed in several steps, including depositing a thin layer of dielectric material and etching holes in appropriate locations of the dielectric layer where portions of the conductive material will be deposited to bridge the interconnect layers. Then a layer of conductive material is deposited across the surface such that a layer of conductive material remains on top of the dielectric layer and the appropriate holes are filled with conductive material. Then standard masking and etching processes are used to remove the excess conductive material corresponding to undesired material that will not be included in the interconnect. For more complicated interconnect structures such as that shown in FIGS. 1A, 2C, 3A, and 3B or for structures that include formation of an antenna or inductive coil such as those shown in FIG. 4B, or 4D, these steps are repeated until the desired structure is formed.

In some embodiments, a single bio-compatible iUHD device such as the device 102 as shown in FIG. 1A is manufactured as described above. Alternatively, multiple bio-compatible iUHD devices may be manufactured at once using a single substrate panel. The substrate panel is formed from a substantially bio-compatible material such as silicon. FIGS. 6A-6D are diagrams 600*a*-600*d* of two iUHD devices that are manufactured using a single substrate panel 618, according to an illustrative embodiment of the invention. Diagrams 600*a*-600*d* depict different stages of the fabrication process. In diagram 600*a*, IC devices 610*a* and 610*b*, 612*a* and 612*b*, and 614*a* and 614*b* have already been coupled into the recesses that will form the respective devices. In addition, dielectric layers 634 and interconnects 620*a*-620*f* have been formed, and portions of the dielectric material 634 above the IC devices 610*a*-*b* have been removed. In contrast to the device 102 in FIG. 1A, which is encapsulated on all sides with the encapsulating layer 130, the device in 600*b* includes layers of bio-compatible material 630 on the top and back surfaces, exposing the side surfaces of the bio-compatible substrate panel 618. In diagram 600*c*, portions of the IC devices 610*a* and 610*b* have been exposed by removal of a portion of the encapsulating layer, while preserving a hermetic seal. Finally, in diagram 600*d*, the substrate panel 618 is singulated into two separate devices (step 456 in FIG. 5). One device includes IC devices 610*a*, 612*a*, and 614*a*, while the other device includes IC devices 610*b*, 612*b*, and 614*b*.

Figure 7:
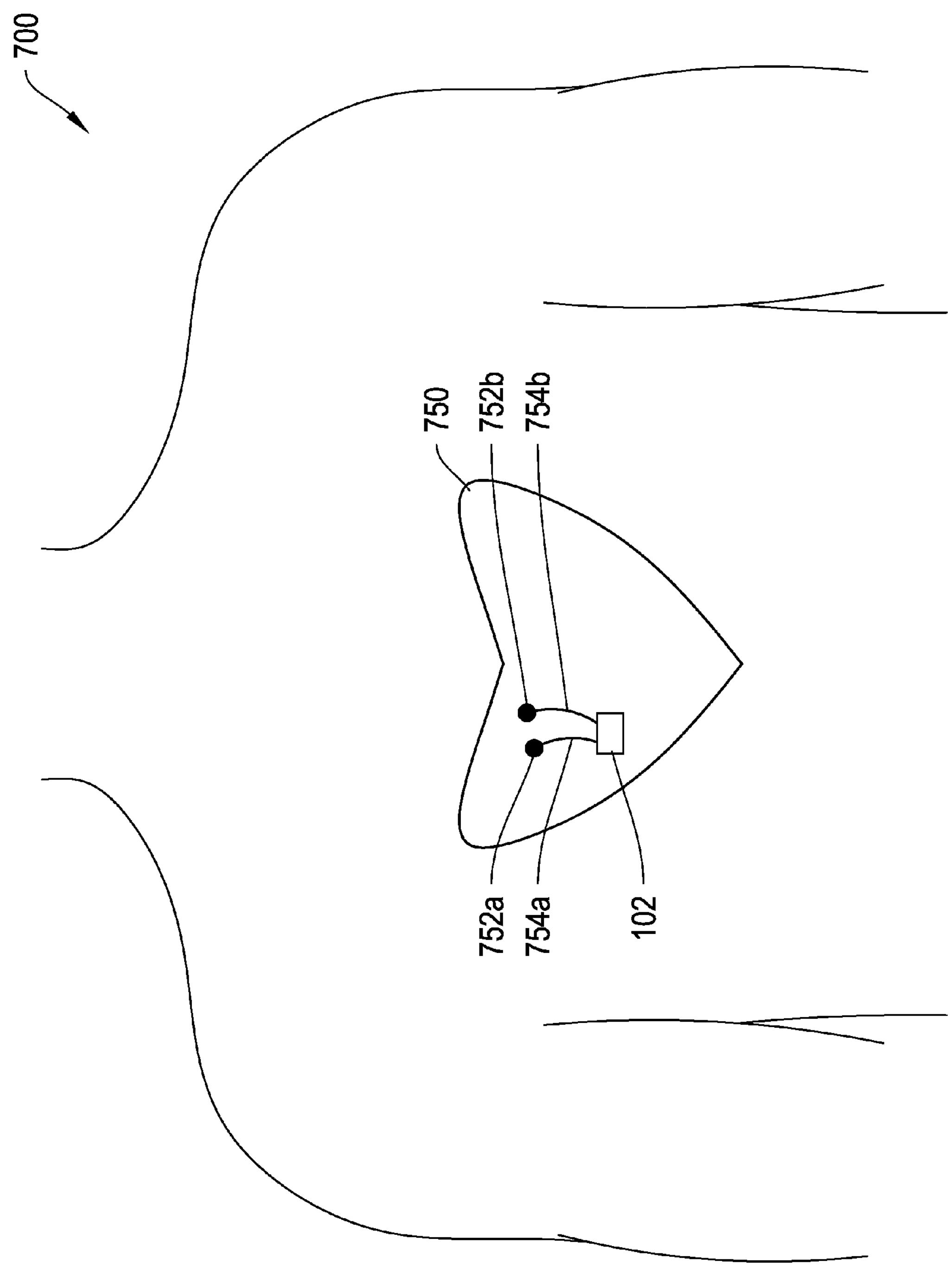
FIG. 7 is a diagram of a bio-implantable hermetic iUHD device implanted in a body, according to an illustrative embodiment of the invention.

FIG. 7 is a diagram 700 of a bio-implantable hermetic iUHD device 102 implanted in a body, according to an illustrative embodiment of the invention. Diagram 700 includes the body's heart 750 and the device 102. Device 102 is an artificial pacemaker that monitors the pulsation of the heart 750 and transmits electrical signals to an area of the heart when appropriate to improve synchronization.

Device 102 is a bio-compatible, implantable, hermetic iUHD device that has been implanted near the heart 750 of the body. Electrode lead 752*a* is a sensor that is positioned on a chamber of the heart 750 and records electrical signals that contain information indicative of contractions of the heart muscle. These electrical signals are transmitted along the electrode wire 754*a* to the device 102, which monitors the heart's contractions and checks for abnormalities in the received signals. When an abnormality occurs (such as an irregular pulse or a long delay between pulses), the device 102 generates and transmits an electrical signal along the electrode wire 754*b* to the electrode lead 752*b*. The electrode lead 752*b* delivers the generated electrical signal to the heart 750, causing the muscle to contract. Thus, device 102 regulates and improves synchronization of the heart muscle contractions.

Applications for device 102 are not limited to artificial pacemakers and may be used for neural recording, neural stimulation, drug delivery, or any application of an implantable medical device. Other examples include cochlear implants, brain implants, spine implants, and retinal implants.

While various embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method of manufacturing an implantable, bio-compatible, integrated circuit device, comprising the steps of:

providing a substrate having a recess formed within the substrate;

coupling an input/output device comprising at least one bio-compatible electrical contact to the substrate in the recess;

coupling a second device within the substrate;

applying a bio-compatible, hermetic insulator to a portion of the input/output device;

encapsulating at least a portion of the implantable device, including the input/output device, with an encapsulating layer of bio-compatible material; and electrically and communicatively directly coupling the input/output device to the second device by an interconnect prior to encapsulating the portion of the implantable device, wherein the second device is configured to process a signal to be transmitted by or received from the input/output device via the interconnect;

exposing, through the encapsulating layer, the at least one bio-compatible electrical contact of the input/output device, such that a hermetic seal is preserved between the encapsulating layer and the layer of bio-compatible, hermetic insulator material around the at least one exposed bio-compatible electrical contact.

2. The method of claim 1, wherein the input/output device comprises a thinned die.

3. The method of claim 1, wherein the input/output device is configured to generate, transmit, receive and/or process electrical signals corresponding to an implant site.

4. The method of claim 1, wherein the encapsulating layer of bio-compatible material comprises titanium.

5. The method of claim 1, comprising forming, prior to encapsulating the implantable device, at least one of an antenna and an inductive coil in communication with at least one of the input/output device and a second device coupled to the substrate.

6. The method of claim 1, comprising coupling, subsequent to the encapsulating step, at least one of an antenna and an inductive coil to a biocompatible electrical contact of the input/output device exposed through the encapsulating layer.

7. The method of claim 1, wherein the bio-compatible, hermetic insulator comprises diamond, ruby, ceramic, sapphire, alumina, glass, or a combination thereof.

8. The method of claim 1, wherein encapsulating the substrate with the encapsulating layer of bio-compatible material comprises depositing the bio-compatible material onto the substrate using sputtering or atomic layer deposition.

9. The method of claim 1, wherein applying the bio-compatible, hermetic insulator comprises applying the insulator to a portion of the input/output device by plasma enhanced chemical vapor deposition or a low-pressure chemical vapor deposition.

10. The method of claim 1, further comprising:

coupling a second input/output device to the substrate in a second recess, and singulating the substrate to form a plurality of separate implantable devices.

* * * * *